(12) United States Patent
Kim et al.

(10) Patent No.: US 10,537,264 B2
(45) Date of Patent: Jan. 21, 2020

(54) G-LOC WARNING METHOD AND SYSTEM USING G-LOC WARNING ALGORITHM

(71) Applicant: Republic of Korea (R.O.K. Air Force Chief of Staff), Gyeryong-si, Chungcheongnam-do (KR)

(72) Inventors: Dongsoo Kim, Seongnam-si (KR); Booyong Choi, Chungcheongbuk-do (KR)

(73) Assignee: REPUBLIC OF KOREA (ROK AIR FORCE CHIEF OF STAFF), Chungcheongnam-Do (KR)

( * ) Notice: Subject to any disclaimer, the term of this patent is extended or adjusted under 35 U.S.C. 154(b) by 0 days.

(21) Appl. No.: 15/312,521

(22) PCT Filed: Aug. 13, 2015

(86) PCT No.: PCT/KR2015/008531
§ 371 (c)(1),
(2) Date: Nov. 18, 2016

(87) PCT Pub. No.: WO2017/026560
PCT Pub. Date: Feb. 16, 2017

(65) Prior Publication Data
US 2018/0140213 A1    May 24, 2018

(51) Int. Cl.
*A61B 5/0488* (2006.01)
*A61B 5/00* (2006.01)
*G08B 21/02* (2006.01)

(52) U.S. Cl.
CPC .......... *A61B 5/0488* (2013.01); *A61B 5/7235* (2013.01); *A61B 5/6813* (2013.01); *A61B 5/7282* (2013.01); *G08B 21/02* (2013.01)

(58) Field of Classification Search
None
See application file for complete search history.

(56) References Cited

U.S. PATENT DOCUMENTS

| 6,265,978 B1 | 7/2001 | Atlas | |
| 2003/0034902 A1* | 2/2003 | Dickau | B64D 45/0015 340/945 |

(Continued)

FOREIGN PATENT DOCUMENTS

KR    2013-0026162 A    3/2013

OTHER PUBLICATIONS

Cornwall, M.W., Krock, L.P. (1992). Electromyographic activity while performing the anti-G straining maneuver during high sustained acceleration. Aviat Space Environ Med. 63(11) 971-5. (Year: 1992).*

(Continued)

*Primary Examiner* — Sean P Dougherty
*Assistant Examiner* — Benjamin S Melhus
(74) *Attorney, Agent, or Firm* — Heslin Rothenberg Farley & Mesiti P.C.; George Blasiak

(57) ABSTRACT

The present invention relates generally to a method for preventing gravity-induced loss of consciousness (G-LOC), which arises from increased acceleration during flight, and more particularly, to a G-LOC warning method and system using a G-LOC warning algorithm, which detects, in advance, risk factors that cause a G-LOC state by monitoring a change in the electromyogram (EMG) signal in real time. According to the G-LOC warning method and system using the G-LOC warning algorithm of the present invention, because information about the EMG signal is measured and collected in real time, changes in the EMG signal of a pilot who is exposed to high levels of acceleration during a flight maneuver are measured and checked on the spot.

15 Claims, 17 Drawing Sheets

(56) References Cited

U.S. PATENT DOCUMENTS

| | | | |
|---|---|---|---|
| 2005/0202375 A1* | 9/2005 | Nevo | A61B 5/00 434/59 |
| 2008/0058621 A1 | 3/2008 | Melker et al. | |
| 2011/0282130 A1 | 11/2011 | Krueger | |
| 2014/0249429 A1 | 9/2014 | Tran | |

OTHER PUBLICATIONS

T. Cho D. Kim et al., "Characteristics of Lower Body EMG Signals during High +Gz Exposure and Generation of Warning Alarm Prior to G-Loc," Aerospace Medicine and Human Performance, vol. 87 (3), 2016.

* cited by examiner

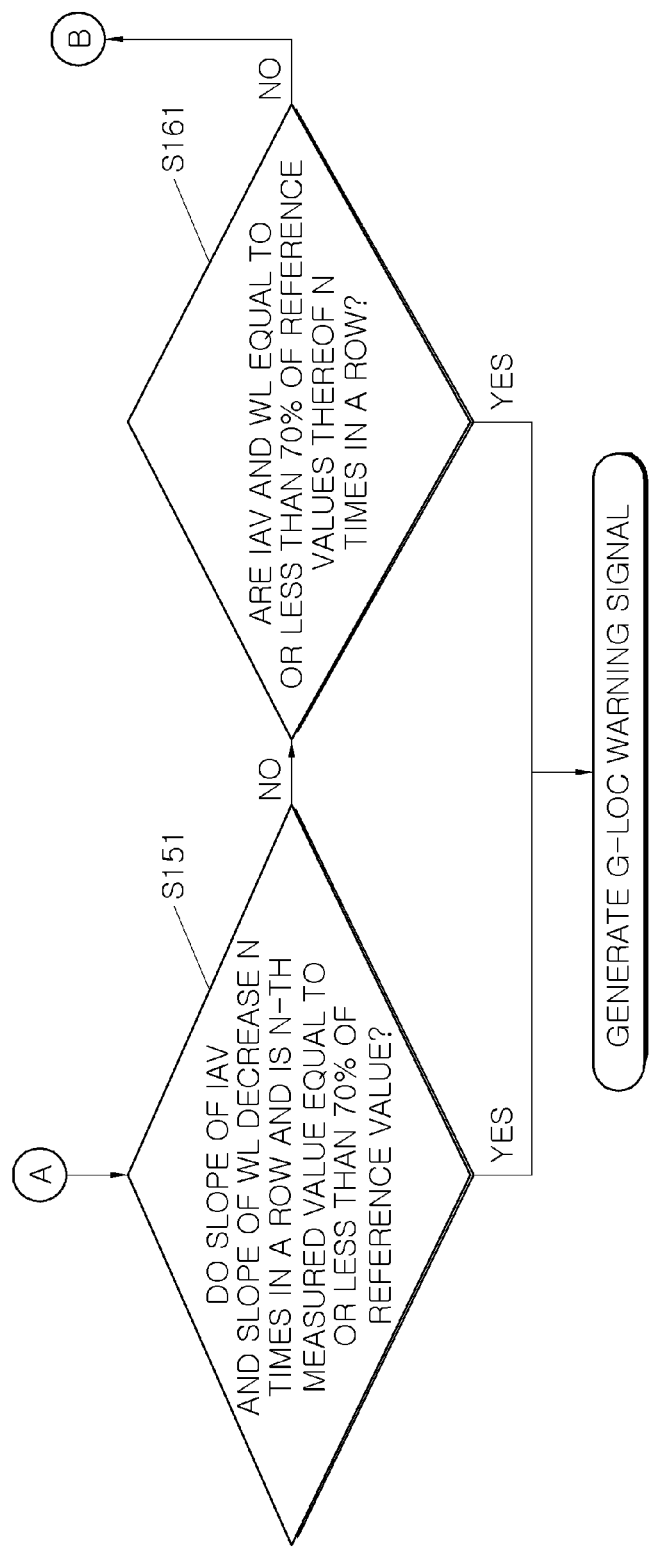

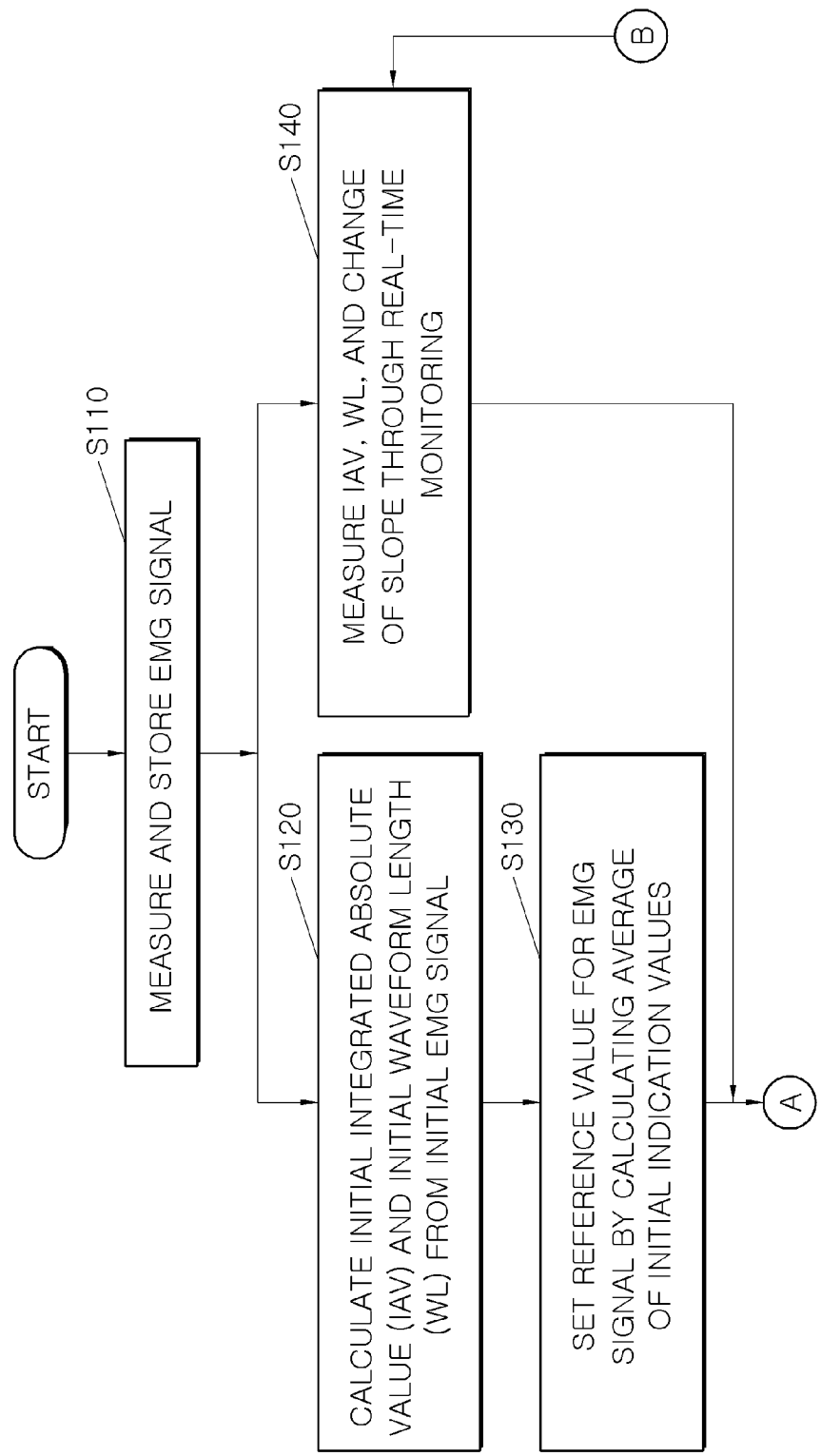

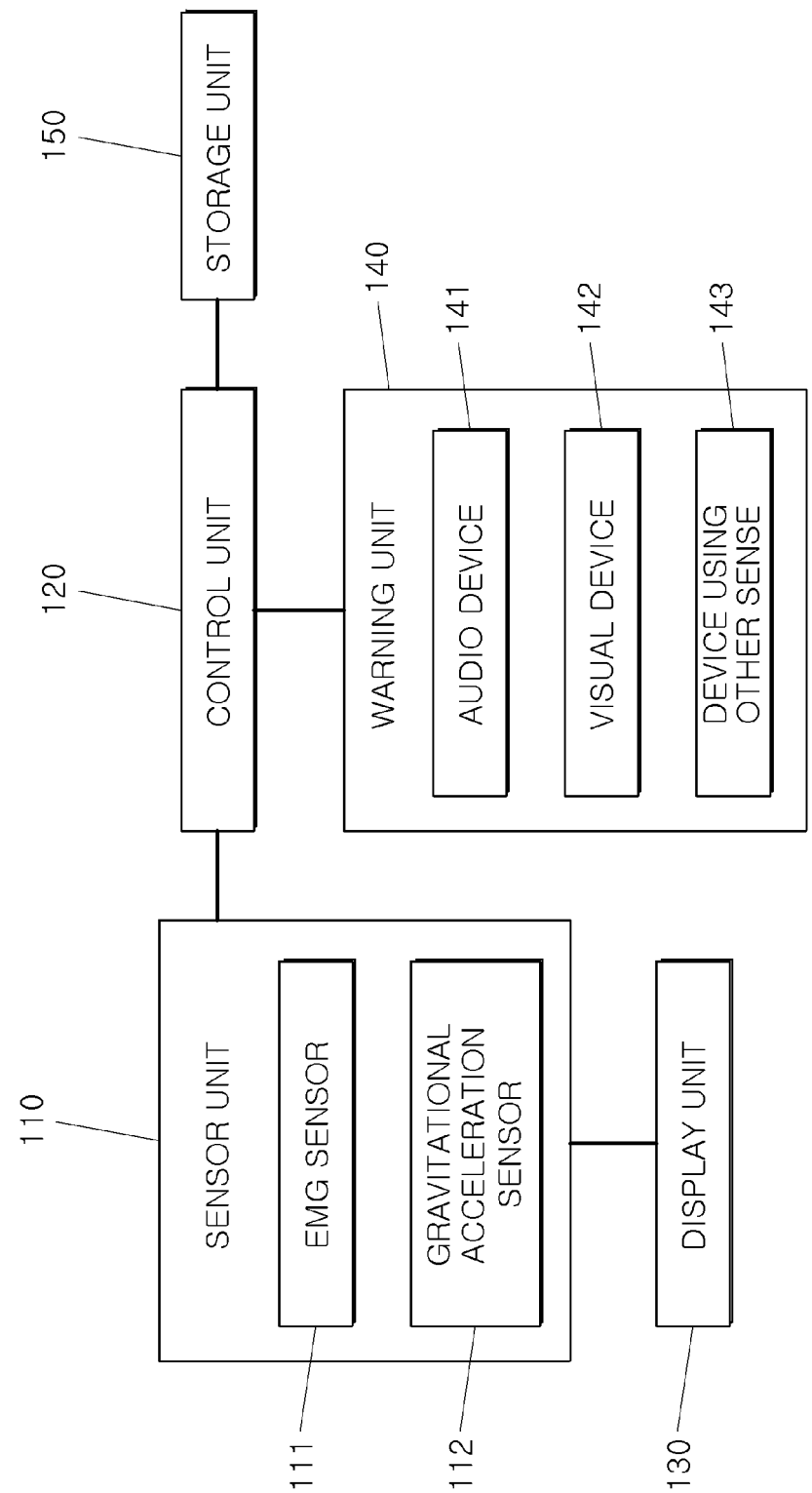

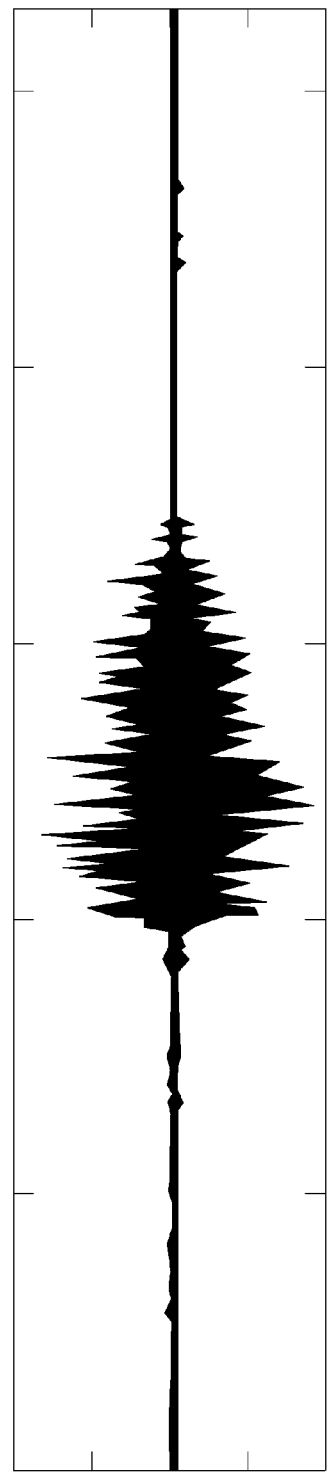

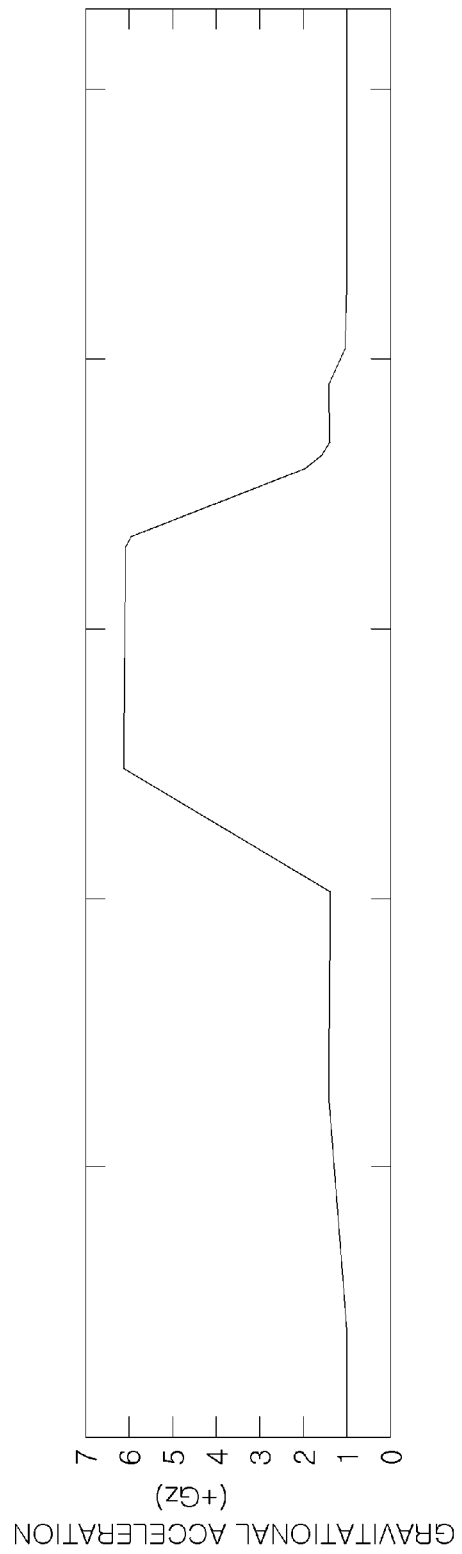

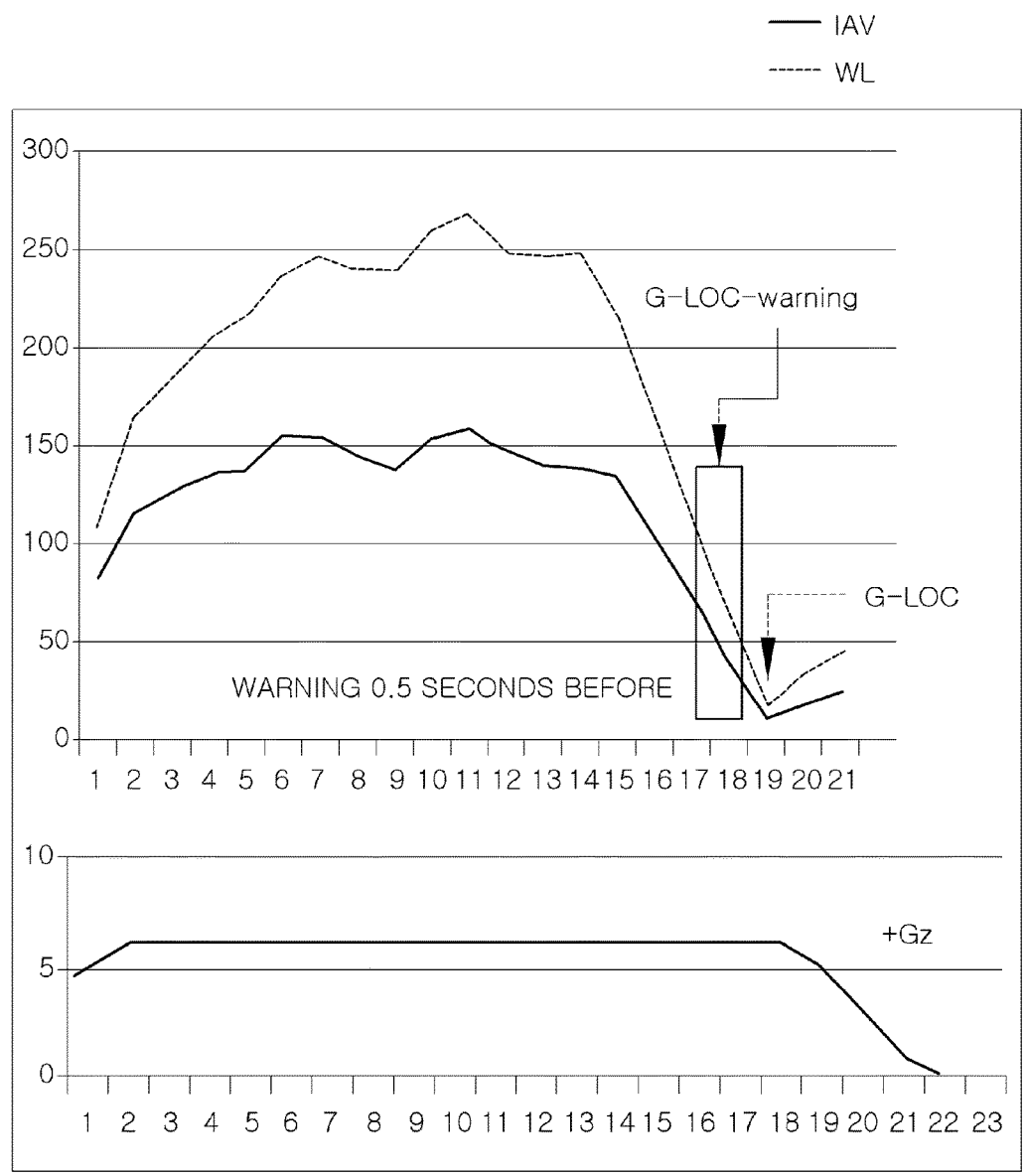

G-LOC WARNING METHOD AND SYSTEM USING G-LOC WARNING ALGORITHM

CROSS-REFERENCE TO RELATED APPLICATIONS

This application claims priority to and is a United States National Phase Application of PCT International Patent Application No.: PCT/KR2015/008531, filed on Aug. 13, 2015, which is incorporated herein by reference in its entirety.

TECHNICAL FIELD

The present invention relates, in general, to a method for preventing gravity-induced loss of consciousness (G-LOC), which arises from increased acceleration during flight, and more particularly, to a G-LOC warning method and system using a G-LOC warning algorithm, which may detect, in advance, risk factors causing a G-LOC state by monitoring changes in an electromyogram (EMG) signal in real time.

BACKGROUND ART

Gravity-induced loss of consciousness (G-LOC) refers to the situation in which a pilot loses consciousness because the amount of blood supplied to his or her head is not maintained due to increased acceleration caused by rapid flight maneuvering.

G-LOC affects the human body, including the cardiovascular system, ocular organs, and the like. Particularly, arterial pressure in the eye is directly affected by G-LOC. A decrease in arterial pressure in the eye means a decrease in the cerebral blood flow to the brain. Generally, the mean pressure in the cerebral arteries decreases by 22 to 25 mmHg for every +1 Gz increase in gravitational acceleration.

Meanwhile, such increased acceleration causes blood to be stagnant in the lower body, and the flow of venal blood to the heart is decreased, thus decreasing cardiac output. The cerebral arterial pressure, which is about 78 mmHg at +1 Gz under normal conditions, falls to −10 mmHg when a person is exposed to +5 Gz of gravitational acceleration, and this is the immediate cause of G-LOC. Also, in response to the decreases in the arterial pressure and the cardiac output, the heart rate sharply increases. Here, +5 Gz is five times the gravitational acceleration of +1 Gz.

The change that is most immediately sensed by a person who is exposed to high levels of acceleration is the change of vision. More specifically, due to the decrease in the pressure of the arteries connected to the eyes, insufficient oxygen is supplied to the retinas, whereby loss of vision may occur. The loss of vision is classified into gray-out, corresponding to loss of peripheral vision, and black-out, corresponding to loss of central vision, according to the phase, and such loss of vision signifies imminent G-LOC.

FIG. 1 shows average G-tolerance. In the state in which no specific apparatus or method is provided, when the G Level of gravitational acceleration (+Gz) rapidly increases from 1 Gz to 6 Gz or higher, or when a person is consistently exposed to gravitational acceleration of 6 Gz or higher, the person may suffer G-LOC within five seconds, as illustrated in FIG. 1.

Therefore, in order to prevent and overcome G-LOC, a pilot (in particular, a fighter pilot) needs to use a method for maintaining a consistent supply of blood to his or her head. As an example of such a method, there are a method of adjusting the angle of a pilot's seat in a fighter plane, a method of quickly contracting the lower limb muscles, such as the muscles of the legs and abdomen, while wearing an anti-G suit, an anti-G straining maneuver (AGSM) for maintaining or increasing the supply of blood to the brain by breathing according to a respiration method called an L-1 Maneuver, and the like.

However, aircraft accidents attributable to G-LOC continue to occur despite various efforts to improve G-tolerance against such increased gravitational acceleration, and reasonable and appropriate solutions have not yet been provided.

DISCLOSURE

Technical Problem

US Patent Application Publication No. 2005-022375 relates to a method and apparatus for warning of G-LOC by detecting G-LOC using a tracking module installed in the helmet of a pilot, which is capable of analyzing and determining the motion of a pilot, such as the head dropping forward and muscle relaxation attributable to G-LOC. However, in the case of a method using the analysis and determination of motion, it is difficult to correctly determine G-LOC before the occurrence of G-LOC.

Therefore, what is required is an algorithm for correctly determining whether a pilot is in a G-LOC state by comparing a normal condition with the G-LOC state and a method for warning of G-LOC in advance by implementing the algorithm.

In consideration of these, an object of the present invention is to provide a warning method and system that may warn of the risk of G-LOC in real time by using an EMG signal as a bio-signal for determining whether a risk of G-LOC exists, particularly using a G-LOC warning algorithm capable of predicting G-LOC based on the real-time analysis of records measured by an EMG device.

Technical Solution

A G-LOC warning method according to an embodiment of the present invention includes measuring an electromyogram (EMG) signal of a muscle using an EMG sensor and storing the EMG signal; setting reference values to an initial reaction value of an integrated absolute value (IAV) and an initial reaction value of a waveform length (WL), calculated based on an initial EMG signal, which is measured for a certain time period from a start of measurement of the EMG signal, and storing the reference values; monitoring the EMG signal in real time using the EMG sensor, calculating the IAV, the WL, a change in a slope of the IAV, and a change in a slope of the WL from the monitored EMG signal, as indication values, and storing the indication values; and determining whether a risk of G-LOC exists by comparing the reference values with the indication values, which are respectively calculated in the setting the reference values and in the calculating, wherein the determining may be configured such that when the slope of the IAV and the slope of the WL, calculated in real time, decrease n times in a row and when each of n-th measured IAV and WL is equal to or less than a certain percentage of the reference value thereof, it is determined that the risk of G-LOC exists and a warning signal is generated.

Also, when it is determined in the determining that there is no risk of G-LOC, if each of the IAV and the WL, measured in real time, is equal to or less than a certain percentage of the reference value thereof n times in a row, it may be determined that the risk of G-LOC exists, and the warning signal may be generated.

Meanwhile, n may be 3.

Also, the measuring may start at 5 G or higher acceleration.

Additionally, the setting the reference values may include calculating the initial reaction value of the IAV and the initial reaction value of the WL based on the initial EMG signal, measured for the certain time period from the start of the measurement of the EMG signal; and calculating and recording an average of the initial reaction value of the IAV and an average of the initial reaction value of the WL.

A G-LOC warning method according to another embodiment of the present invention includes measuring an electromyogram (EMG) signal of a muscle using an EMG sensor and storing the EMG signal; setting reference values to an initial reaction value of an integrated absolute value (IAV) and an initial reaction value of a waveform length (WL), calculated based on an initial EMG signal, measured for a certain time period from a start of measurement of the EMG signal, and storing the reference values; monitoring the EMG signal in real time using the EMG sensor, calculating the IAV, the WL, and changes in slopes of the IAV and WL from the monitored EMG signal, as indication values, and storing the indication values; and determining whether a risk of G-LOC exists by comparing the reference values with the indication values, respectively calculated in the setting the reference values and in the calculating, wherein the determining may be configured such that when each of the IAV and the WL, measured in real time, is equal to or less than a certain percentage of the reference value thereof n times in a row, it is determined that the risk of G-LOC exists and a warning signal is generated.

Also, when it is determined in the determining that there is no risk of G-LOC, if the slope of the IAV and the slope of the WL, calculated in real time, decrease n times in a row and if each of n-th measured IAV and WL is equal to or less than a certain percentage of the reference value thereof, it may be determined that the risk of G-LOC exists and a warning signal may be generated.

Meanwhile, n may be 3.

Also, the measuring may start at 5 G or higher acceleration.

Additionally, the setting the reference values may include calculating the initial reaction value of the IAV and the initial reaction value of the WL based on the initial EMG signal, measured for the certain time period from the start of the measurement of the EMG signal; and calculating and recording an average of the initial reaction value of the IAV and an average of the initial reaction value of the WL.

A G-LOC warning system according to an embodiment of the present invention may include a sensor unit 110, including an EMG sensor, for measuring an EMG signal by being affixed on a part of a body of a user; a control unit 120 for setting reference values using an initial reaction value of an integrated absolute value (IAV) and an initial reaction value of a waveform length (WL) based on the measured EMG signal, for calculating the IAV, the WL, a change in a slope of the IAV, and a change in a slope of the WL as indication values by monitoring the EMG signal in real time using the EMG sensor, and for determining whether a risk of G-LOC exists through a series of determination processes using the reference values and the indication values; a display unit 130 for receiving the EMG signal and displaying the EMG signal as a waveform outside; and a warning unit 140 for receiving a warning signal output from the control unit 120 and warning the user whether a risk exists using an audible means and a visual means.

The G-LOC warning system may further include a storage unit 150 for storing information associated with G-LOC, such as the EMG signal, which is measured in the sensor unit and input to the control unit 120, the set reference values, the calculated indication values, and the like.

When the slope of the IAV and the slope of the WL, calculated in real time, decrease n times in a row and when each of n-th measured IAV and WL is equal to or less than a certain percentage of the reference value thereof, the control unit may determine that the risk of G-LOC exists and output the warning signal to the warning unit.

When the control unit of the G-LOC warning system of the present invention determines that there is no risk of G-LOC, if each of the IAV and the WL, measured in real time, is equal to or less than a certain percentage of the reference value thereof n times in a row, the control unit may determine that the risk of G-LOC exists and output the warning signal to the warning unit.

Also, when each of the IAV and the WL, measured in real time, is equal to or less than a certain percentage of the reference value thereof n times in a row, the control unit of the G-LOC warning system of the present invention may determine that the risk of G-LOC exists and output the warning signal to the warning unit.

When the control unit determines that there is no risk of G-LOC, if the slope of the IAV and the slope of the WL, calculated in real time, decrease n times in a row and if each of the n-th measured IAV and WL is equal to or less than a certain percentage of the reference value thereof, the control unit may determine that the risk of G-LOC exists and output the warning signal to the warning unit.

Advantageous Effects

According to the G-LOC warning method and system using the G-LOC warning algorithm of the present invention, because information about an EMG signal is measured and collected in real time, changes in the EMG signal of a pilot who is exposed to high levels of acceleration during flight maneuvers may be measured and checked on the spot.

Also, because a G-LOC warning algorithm includes criteria for comparison, the present invention has the effect of improving the reliability of the verification of an Integrated Absolute Value (IAV) and a Waveform Length (WL), which are measured in real time.

Also, the present invention may evaluate both the force of muscle contraction and muscle fatigue at the same time by analyzing an EMG signal, and because a G-LOC state may be continuously predicted in real time, a pilot may be prevented from injury when exposed to high levels of acceleration, and the performance of AGSM may be evaluated.

Also, the G-LOC warning method and system using the G-LOC warning algorithm of the present invention has the effects of reducing the incidence of aircraft accidents and saving the life of a pilot by inducing an aircraft to fly stably before crashing by quickly detecting G-LOC in advance.

DESCRIPTION OF DRAWINGS

FIGS. 2A, 2B, 3A, and 3B show a G-LOC warning method using a G-LOC warning algorithm according to an embodiment of the present invention;

FIG. 4 is a block diagram of a G-LOC warning system according to an embodiment of the present invention;

FIGS. 5A, 5B, and 5C are graphs illustrating a change in an EMG signal when a G-LOC situation occurs;

FIGS. 8A, 8B, 8C, 8D, 8E, and 8F are graphs illustrating a change in a measured EMG signal according to an embodiment of the present invention.

BEST MODE

Figure 1:
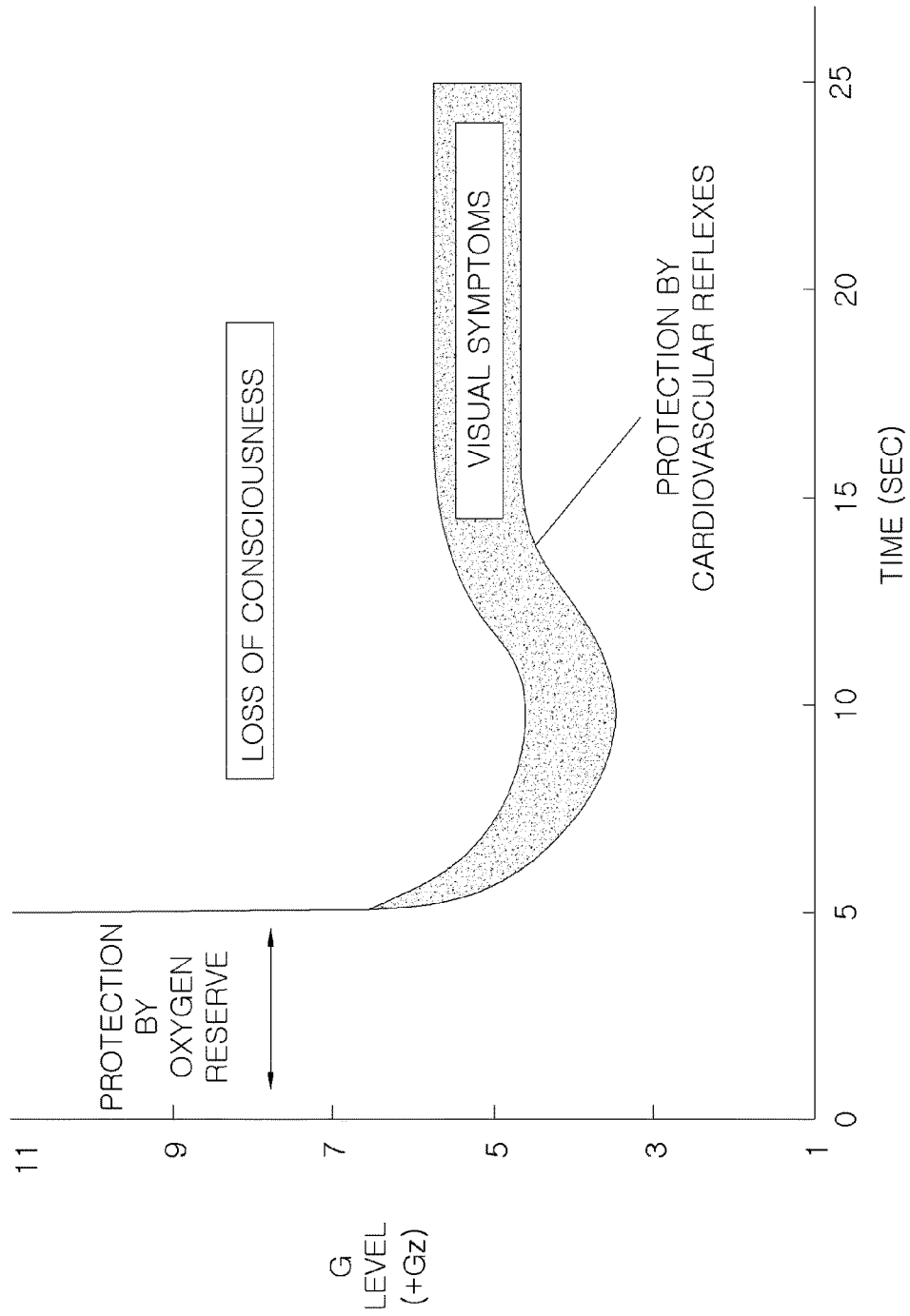
FIG. 1 is a graph illustrating the G-tolerance of an average person over time.

Hereinafter, an embodiment of the present invention will be described in detail with reference to the accompanying drawings, but this embodiment is merely an example. Accordingly, the present invention is not limited to the embodiment, and may be implemented in various forms by those skilled in the art to which the present invention pertains.

Also, in the following description, it should be apparent to those skilled in the art that the present invention may be embodied without specific details such as detailed configurations or components.

In a G-LOC warning algorithm of the present invention, an electromyogram (EMG) signal, which is a signal generated when muscles contract, is measured using an EMG sensor. Specifically, a surface EMG signal, generated in muscles near electrodes placed on the skin of a subject, is measured.

The regions in which the EMG is to be measured according to an embodiment may be the back of a pilot's neck, the abdomen and the legs, and may be a part in which an EMG signal, which changes in response to the increased acceleration, can be measured. Desirably, the EMG signal from the calf muscles may be measured, and more desirably, the EMG signal from the gastrocnemius muscle may be measured, whereby the force of skeletal muscle contraction may be measured upon exposure to high levels of acceleration.

In the G-LOC warning algorithm, when acceleration becomes equal to or greater than 5 G, the EMG signal from a muscle is measured using an EMG sensor and is then stored, and an indication value is calculated using a certain equation based on the measured EMG signal.

As an indication value with which G-LOC may be predicted, there are the root mean square (RMS) of the amplitude of an EMG signal, the integrated absolute value (IAV), the mean absolute value (MAV), the slope sign change (SSC), the waveform length (WL), the zero crossing (ZC), the median frequency, and the like.

Here, the RMS, the IAV, and the MAV are indication values for evaluating the force of muscle contraction, and the SSC, the WL, the ZC, and the median frequency may be used as indication values for evaluating both the force of muscle contraction and muscle fatigue. Among these indication values, an indication value that meaningfully changes before and after G-LOC may be analyzed.

Each of these indication values may be calculated using the following equations from Equation (1) to Equation (6) based on the measured EMG signal.

The root mean square (RMS) is calculated using the following Equation (1):

$$\text{RMS} = \sqrt{\frac{1}{N}\sum_{n=1}^{N} x_n^2} \qquad (1)$$

The integrated absolute value (IAV) may be calculated using the following Equation (2):

$$IAV = \sum_{n=1}^{N} |x_n| \qquad (2)$$

Also, the mean absolute value (MAV), which is acquired by averaging the IAV, may be calculated using the following Equation (3):

$$MAV = \frac{1}{N}\sum_{n=1}^{N} |x_n| \qquad (3)$$

The waveform length (WL) may be calculated using the following Equation (4):

$$WL = \sum_{n=1}^{N-1} |x_{n+1} - x_n| \qquad (4)$$

The slope sign change (SSC) may be calculated using the following Equation (5):

$$SSC = \sum_{n=2}^{N-1} [f\{x_n - x_{n-1}\} \times \{x_n - x_{n-1}\}] \qquad (5)$$

$$\text{where } f(x) = \begin{cases} 1, & \text{if } x \geq \text{threshold} \\ 0, & \text{otherwise} \end{cases}$$

The zero crossing (ZC) may be calculated using the following Equation (6):

$$ZC = \sum_{n=1}^{N-1} [\text{sgn}(x_n \times x_{n-1}) \cap |x_n - x_{n+1}| \geq \text{threshold}] \qquad (6)$$

$$\text{where } \text{sgn}(x) = \begin{cases} 1, & \text{if } x \geq \text{threshold} \\ 0, & \text{otherwise} \end{cases}$$

Hereinafter, first, the G-LOC warning algorithm of the present invention will be described in detail.

The G-LOC warning algorithm starts when the acceleration becomes equal to or greater than 5 G, and an EMG signal measured using an EMG sensor is stored. Here, as the initial reaction values in the measured EMG signal, indication values are calculated using the above-described equations based on the EMG signal, which is measured for 3 seconds. Then, a reference value is set to a value that is acquired by averaging the calculated indication values. Here, it is desirable for the reference value to be a value acquired by averaging the IAV or a value acquired by averaging the WL.

Meanwhile, the indication values, calculated based on the EMG signal, which is measured in real time, and the slope of the indication values are detected. Here, each of the indication values may be monitored, and monitoring may be performed using 3-second windows with an overlap of 0.5 seconds, which are set in consideration of the wavelength of the EMG signal. After monitoring of the EMG signal is performed, the results, processed in real-time, may be displayed and checked.

Subsequently, whether a risk of G-LOC exists is determined based on the reference value, the indication values, and the changes in the slopes of the indication values, which are calculated in real time. When a signal, generated depending on the determination, is received, if the signal corresponds to a critical condition in which a person may enter a G-LOC state, a warning signal is generated, whereby a warning may be given through various senses, including the sense of hearing and the sense of sight.

Also, when it is determined that there is no risk of G-LOC, or after the warning signal is generated, the measurement of an EMG signal and evaluation of the risk of G-LOC may be continuously performed by monitoring the EMG signal in real time.

In connection with the above description, a G-LOC warning method of the present invention will be described in detail. The method may be implemented as a first embodiment and a second embodiment depending on the method for determining whether G-LOC is to occur based on the IAV and WL, selected from among the indication values.

Figure 2A:
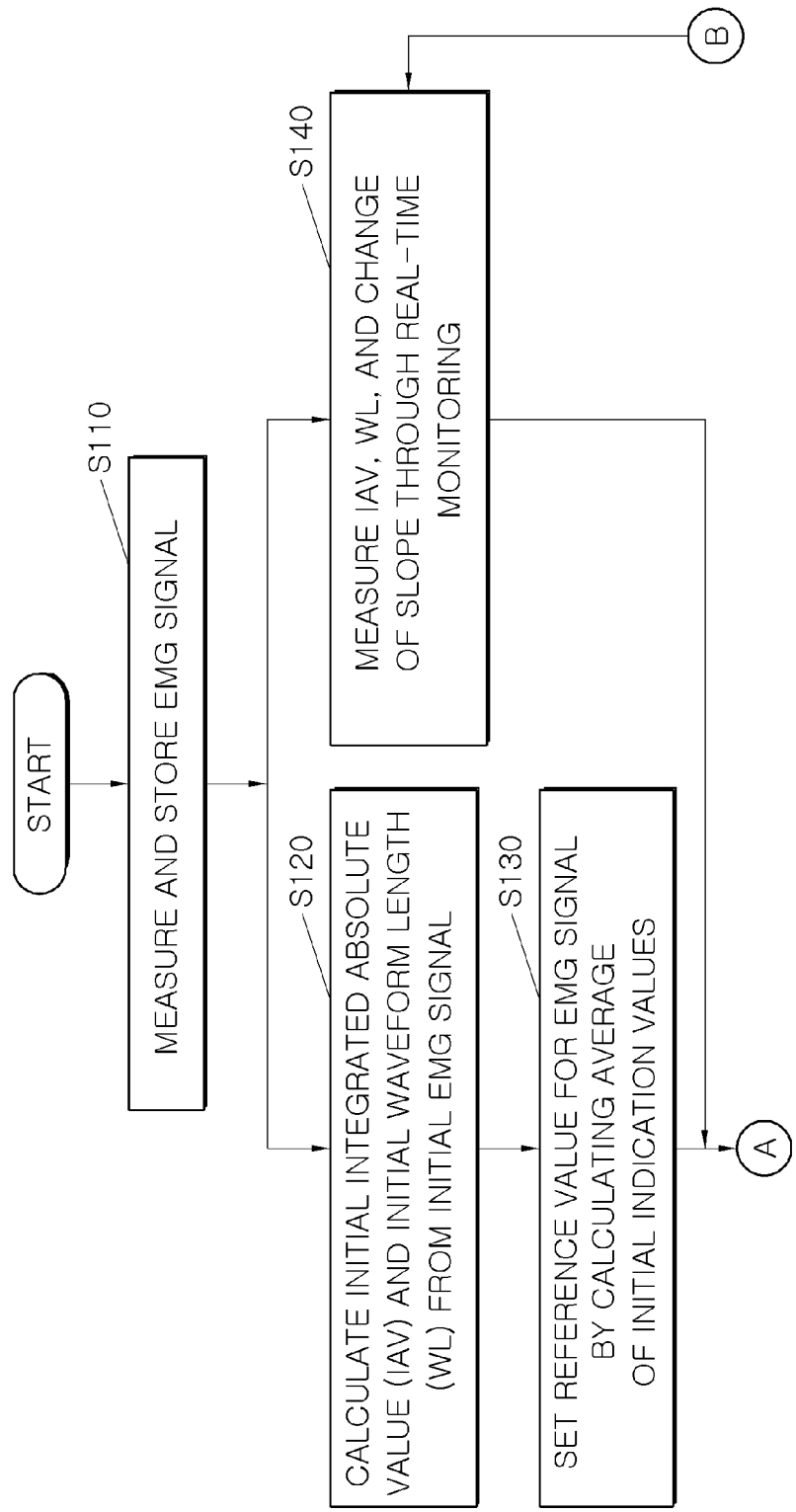

As illustrated in FIGS. 2A, and 2B, in a step of measuring an EMG signal in the first embodiment, when acceleration equal to or greater than 5 G is applied, an EMG signal is measured using an EMG sensor, and is then stored at step S110. In a step of setting a reference value for an EMG signal, the initial reaction values of the IAV and the initial reaction values of the WL are calculated at step S120 using the initial EMG signal, which is measured for 3 seconds from the start of measurement, and the reference values are set by averaging the initial reaction values of the IAV and by averaging the initial reaction values of the WL at step S130.

Here, the measured EMG signal is the initial reaction value, and may be measured using 1-second windows with an overlap of 0.5 seconds, which are set in consideration of the wavelength of the EMG signal.

Meanwhile, in a step of monitoring an EMG signal, the EMG signal may be monitored in real time using the EMG sensor, and the IAV, the WL, and changes in the slopes of the IAV and the WL are calculated at step S140. Monitoring may be performed in real time using 3-second windows with an overlap of 0.5 seconds in consideration of the wavelength of the EMG signal.

Then, in a step of determining whether a risk of G-LOC exists, whether the current state satisfies the conditions for G-LOC is determined by comparing each of the reference values calculated in the step of setting the reference value for the EMG signal with each of the indication values calculated in the step of monitoring the EMG signal. More specifically, in the result of the monitoring, when the slopes of the IAV and the WL, which are measured in real time, decrease n times in a row, and when each of the n-th measured values is equal to or less than 70% of the reference value thereof, it is determined that the risk of G-LOC exists, and a warning may be given at step S151. If it is determined from the criteria that there is no risk of G-LOC, whether the IAV and the WL, measured in real time, are equal to or less than 70% of the reference values thereof n times in a row is checked, and if so, it is determined that there is the risk of G-LOC, and thus a warning is given at step S161, as shown in FIG. 2B. Here, it is desirable to set n to 3.

Figure 3B:
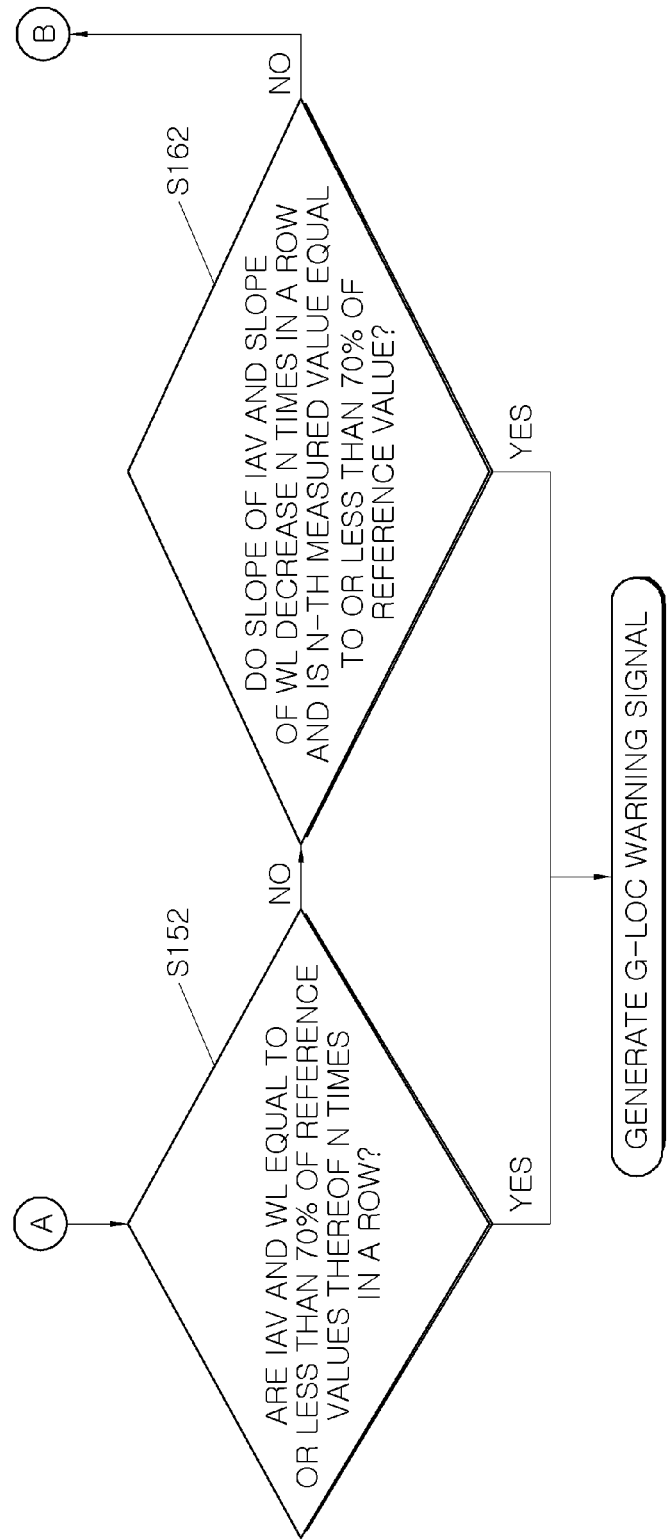

In the second embodiment, the same processes are performed as in the first embodiment. However, the step of determining whether the risk of G-LOC exists is performed in a way other than that in the first embodiment, as shown in FIG. 3B. Specifically, when the IAV and the WL, measured in real time, are equal to or less than 70% of the reference values thereof n times in a row, it is determined that the risk of G-LOC exists, and thus a warning is given at step S152.

Also, when it is determined from the above criterion that there is no risk of G-LOC, when the slopes of the IAV and the WL, measured in real time, decrease n times in a row and when each of the n-th measured values is equal to or less than 70% of the reference value thereof, it is determined that the risk of G-LOC exists, thus a warning is given at step S162. Here, desirably, n may be 3.

As illustrated in FIG. 4, a G-LOC warning system according to the present invention may include a sensor unit 110, a control unit 120, a display unit 130, a warning unit 140, and a storage unit 150.

The sensor unit 110 includes an EMG sensor 111 and a gravitational acceleration sensor 112. The EMG sensor 111 measures an EMG signal by being affixed on a part of the body of a user, and the part of the body may be the back of a pilot's neck, the abdomen, or the calves. More desirably, the EMG signal from a calf muscle may be measured. Particularly, if the force of skeletal muscle contraction in response to exposure to acceleration is evaluated from the EMG signal measured from the gastrocnemius muscle, the accuracy of the evaluation may be improved.

The gravitational acceleration sensor 112 is a sensor that is capable of measuring the gravitational acceleration applied to a user in real time.

The control unit 120 receives the EMG signal and processes the signal according to the above-mentioned G-LOC warning method. More specifically, the G-LOC warning method is the method illustrated in FIGS. 2A and 2B, and may be configured such that, based on the EMG signal measured by the sensor unit 110, the initial reaction values of the IAV and the initial reaction values of the WL are calculated at step S120; the average of the calculated initial reaction values of the IAV and the average of the calculated initial reaction values of the WL are calculated and set as reference values at step S130; the IAV, the WL, and changes in the slopes of the IAV and the WL are calculated as indication values at step S140 by monitoring the EMG signal in real time using the EMG sensor; a series of determination processes is performed using the reference values and the indication values (steps S151 and S161); and a G-LOC warning signal is output depending on the determination. Also, as shown in FIG. 3B, the determination processes for outputting a G-LOC warning signal in the signal processing method may be performed in the opposite order (steps S152 and S162) of the determination processes illustrated in FIG. 2B. Here, the control unit may be a device that is capable of information processing, such as a computer, a laptop, or the like.

Because the G-LOC warning method performed by the control unit 120 of the G-LOC warning system is the same as the above-described G-LOC warning method using the G-LOC warning algorithm according to an embodiment of the present invention, the description thereof will be omitted.

The display unit 130 includes a display means for receiving the EMG signal measured by the sensor unit and displaying the EMG signal outside, and may display the measured EMG signal as a waveform.

The warning unit 140 receives a warning signal output from the control unit and warns a user using a visual means and an audible means. The warning unit 140 may warn a user whether there is a risk using an audio device 141, which generates an alarm, a visual device 142, which flickers warning light, and devices using the other senses 143, and effectively reminds a user, who is at risk of losing consciousness, whether a risk exists by being arranged in a place that may be easily noticed by the user.

Meanwhile, the storage unit 150 may store information associated with G-LOC, such as the EMG signal, which is measured by the sensor unit and input to the control unit 120, the set reference values, the calculated indication values, and the like, therein.

The embodiment of the present invention is accomplished targeting 47 Korean air force pilots whose age ranges from 27 to 40, and the EMG signal is measured using circular electrodes placed at intervals of 5 cm on the gastrocnemius muscle and the soleus muscle.

Figure 5B:
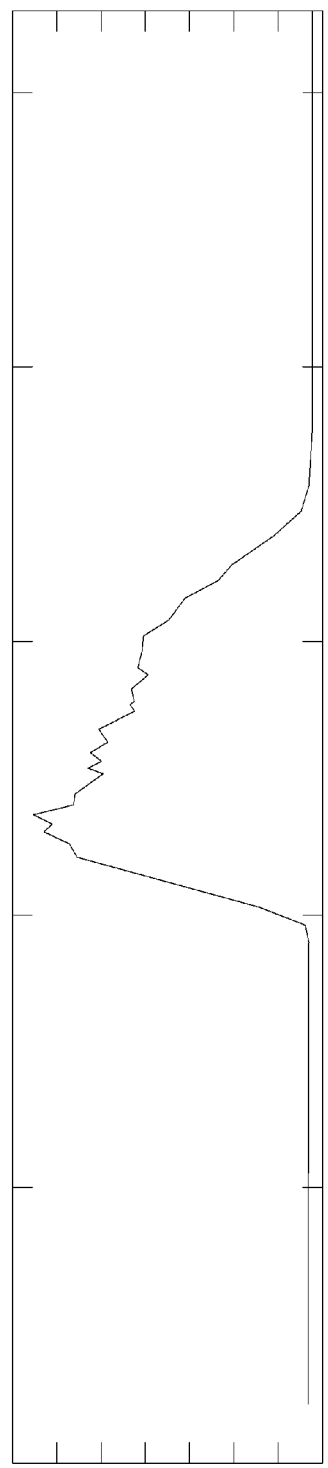

When G-LOC occurs due to the exposure to high levels of acceleration, the peak of the EMG signal tends to decrease over time, as illustrated in FIG. 5A, and this tendency may be confirmed from the moving average of the EMG signal, as shown in FIG. 5B. It is confirmed that G-LOC occurs if the EMG signal is equal to or less than 0.5 uV on average.

Figure 6:
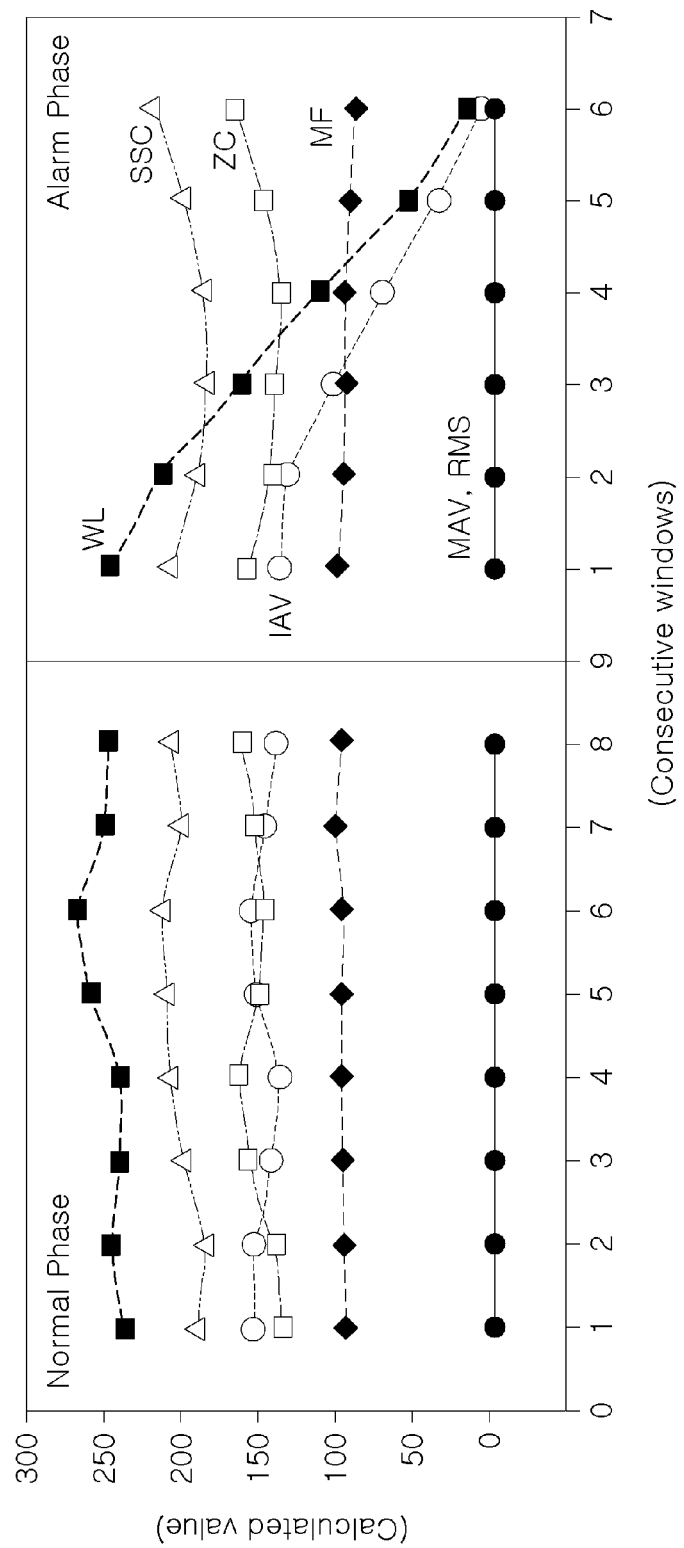
FIG. 6 is a graph illustrating a change in a calculated indication value according to an embodiment of the present invention.
Figure 7:
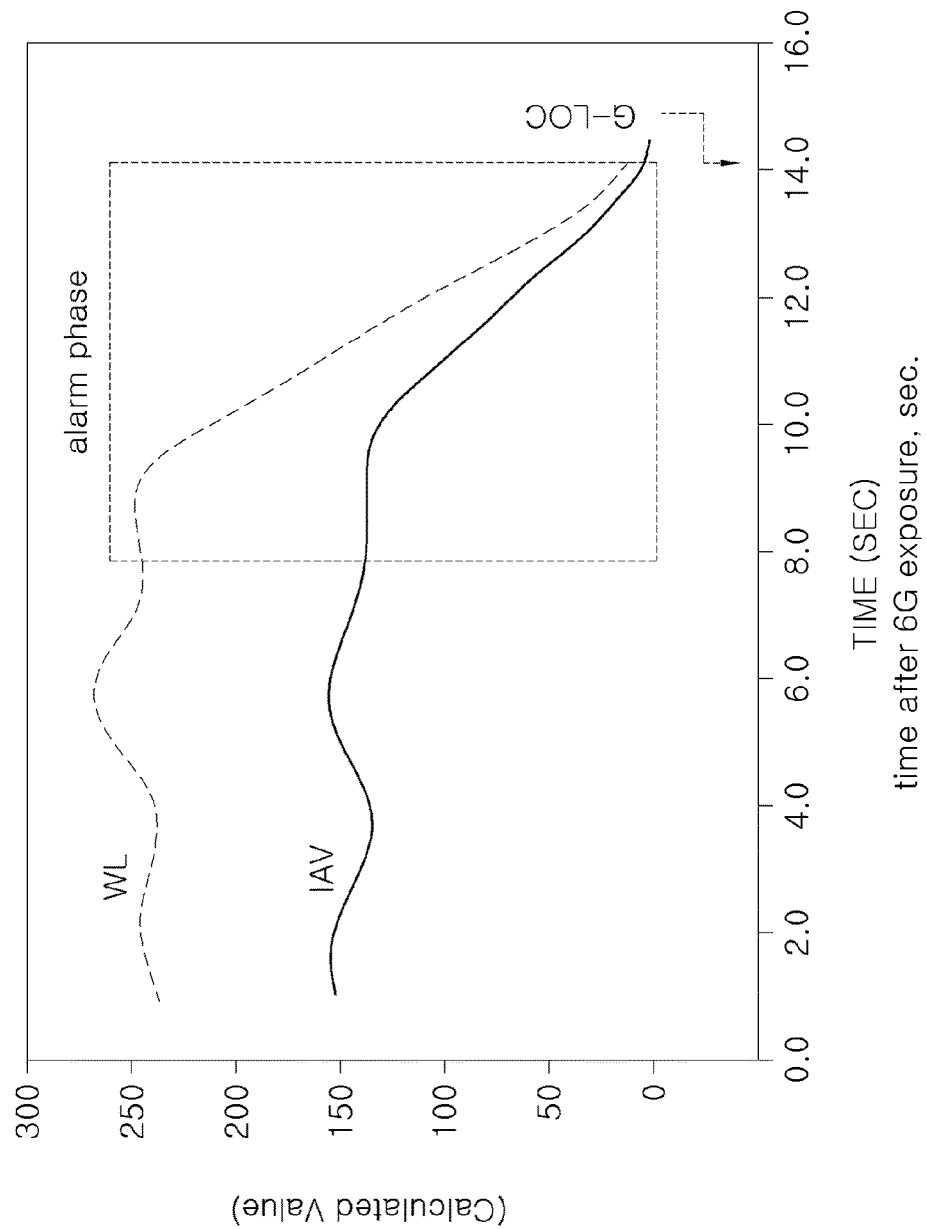
FIG. 7 is a graph illustrating a change in an integrated absolute value (IAV) and a change in a waveform length (WL), calculated according to an embodiment of the present invention.

FIG. 6 and FIG. 7 are graphs in which an EMG signal measured from the calf muscle of a subject is analyzed according to an embodiment of the present invention.

FIG. 6 shows certain reference values calculated based on the measured EMG signal and changes in the RMS, the IAV, the MAV, the SSC, the WL, the ZC, and the MF, which are measured at intervals of 0.5 seconds. Particularly, it is confirmed that the IAV and the WL noticeably decrease in the alarm phase, which corresponds to 3 seconds before the subject enters a G-LOC state.

Also, FIG. 7 shows the result of the consecutive measurement of only the IAV and the WL based on the same data as in FIG. 6. As illustrated, when a subject is exposed to acceleration of 6 G, the IAV and the WL decrease in the alarm phase before the subject enters a G-LOC state.

FIGS. 8A to 8F are graphs illustrating the change in the EMG signal measured in each of the subjects according to an embodiment of the present invention. As shown in FIGS. 8A to 8F, it is confirmed that, according to the G-LOC warning algorithm, a G-LOC warning signal sounds 0.5 to 3.5 seconds before the occurrence of G-LOC depending on the EMG signal measured from each of the subjects when they are exposed to acceleration of 6 G.

Figure 8A:
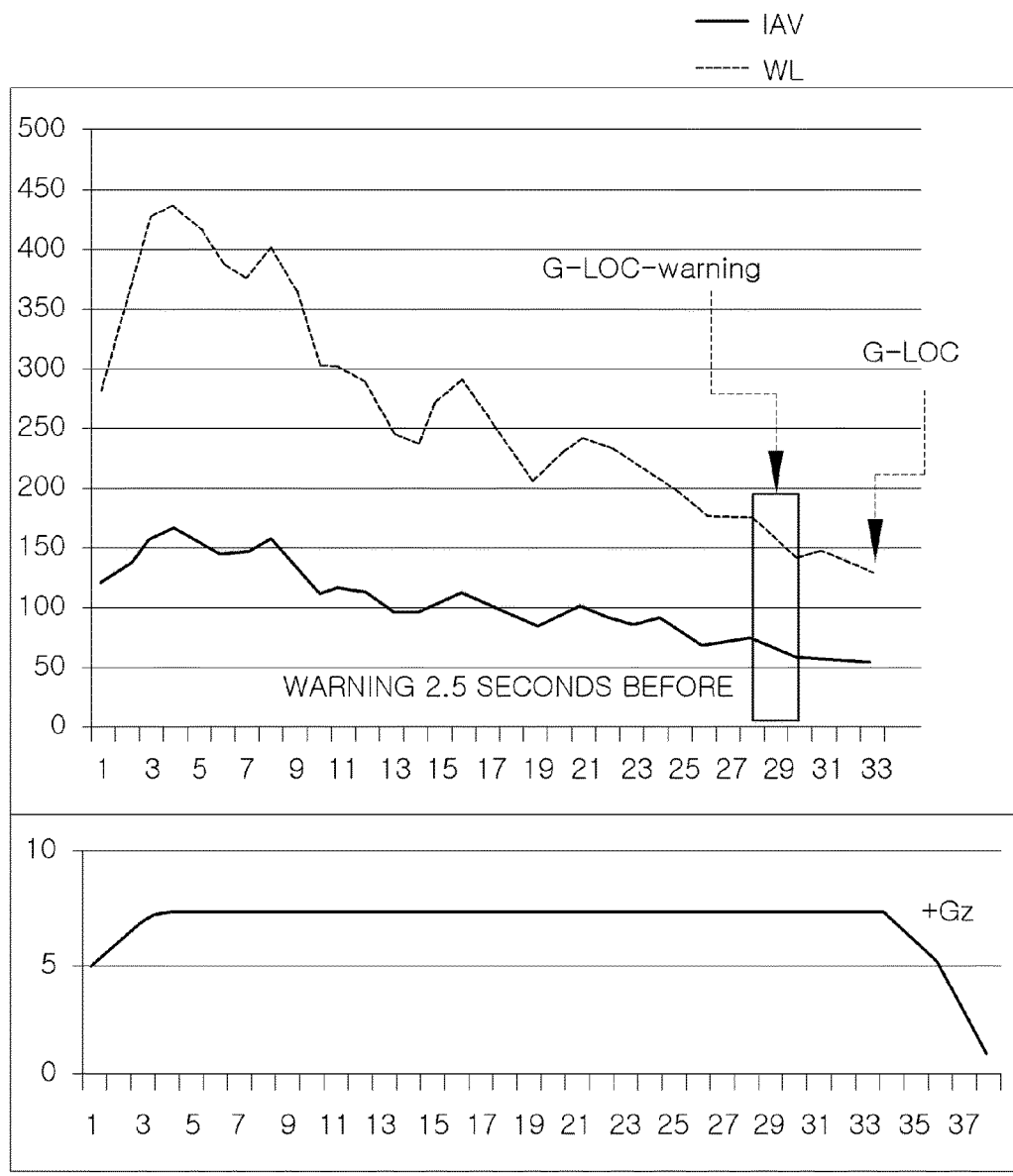
Figure 8C:
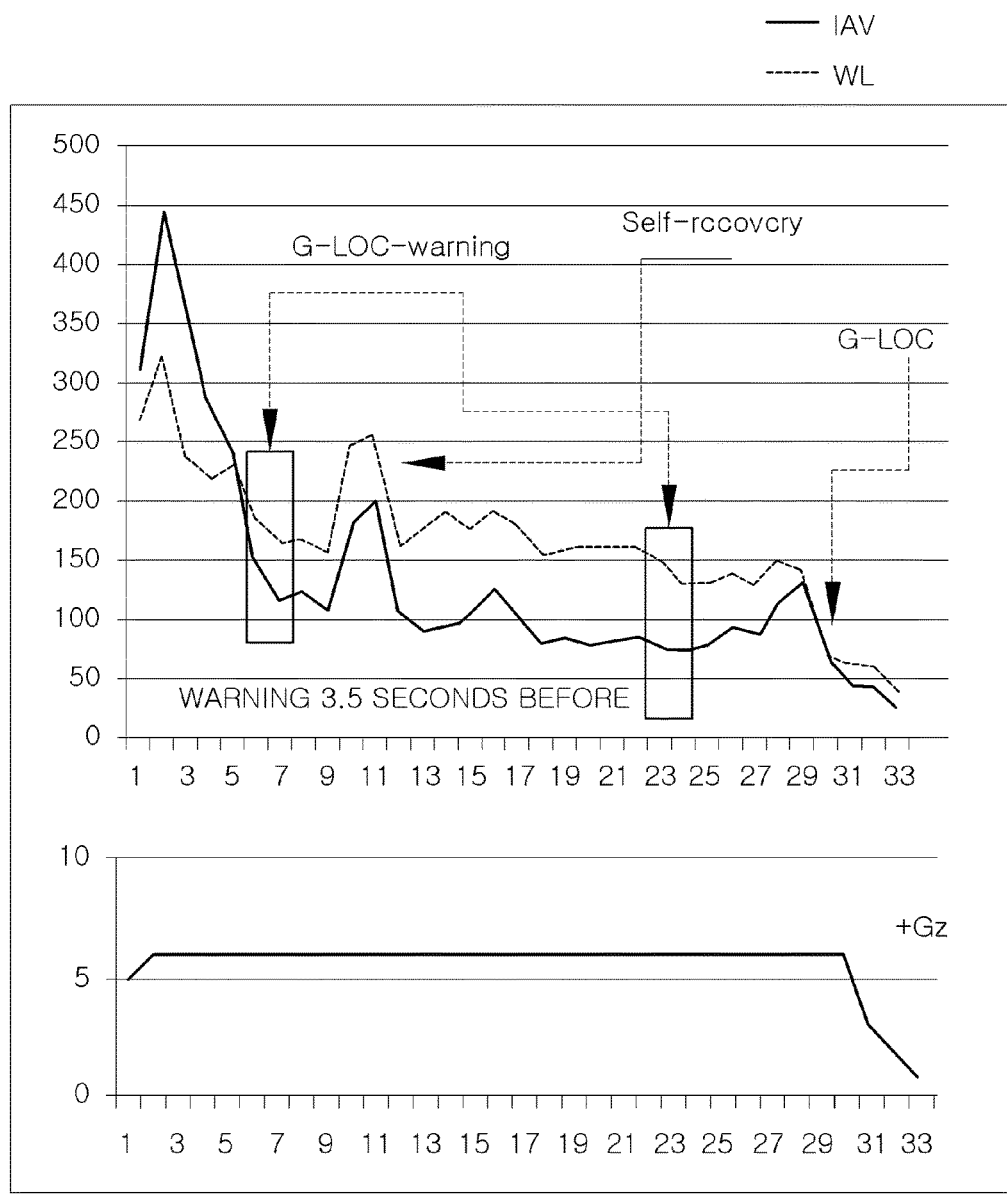
Figure 8D:
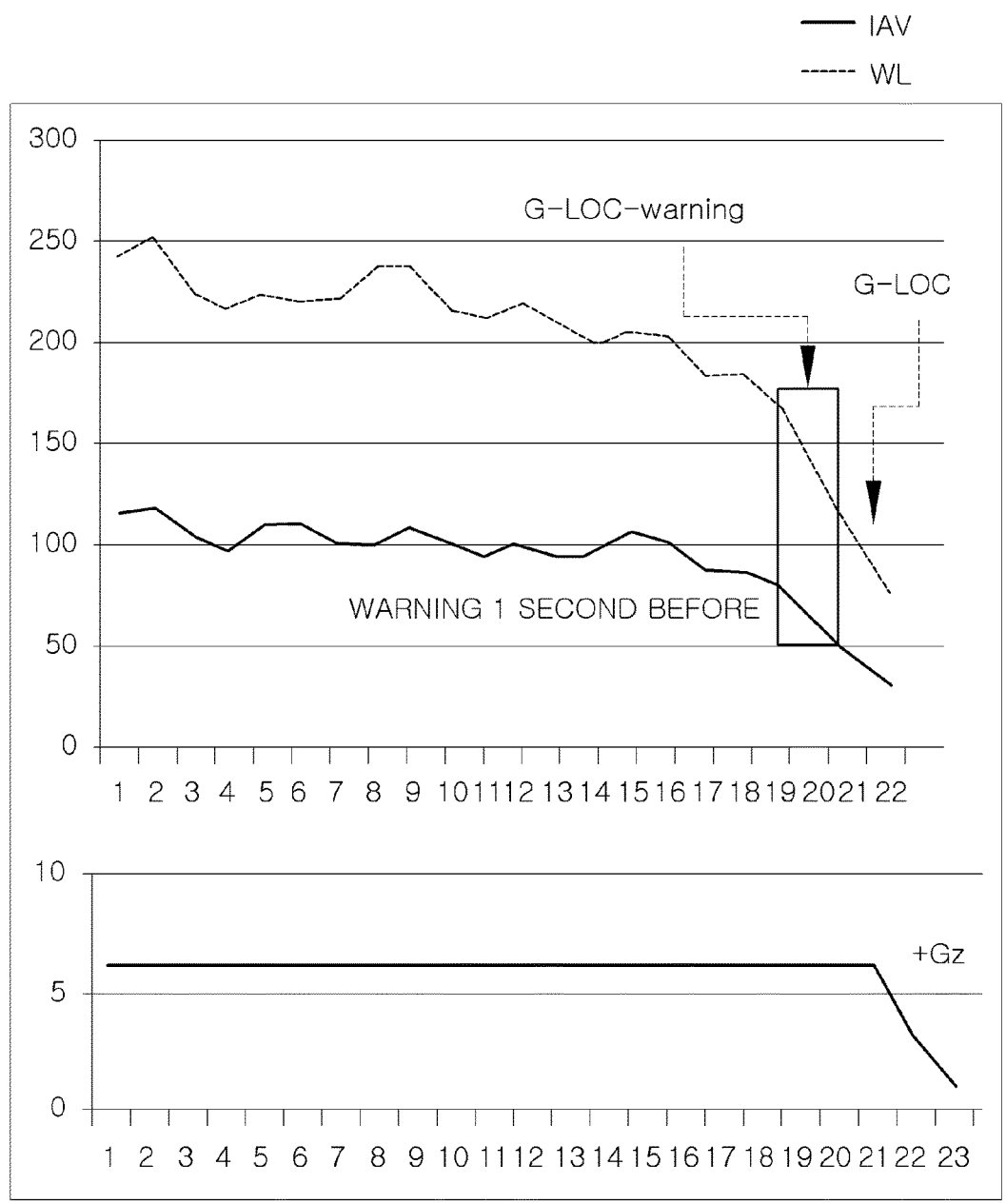
Figure 8E:
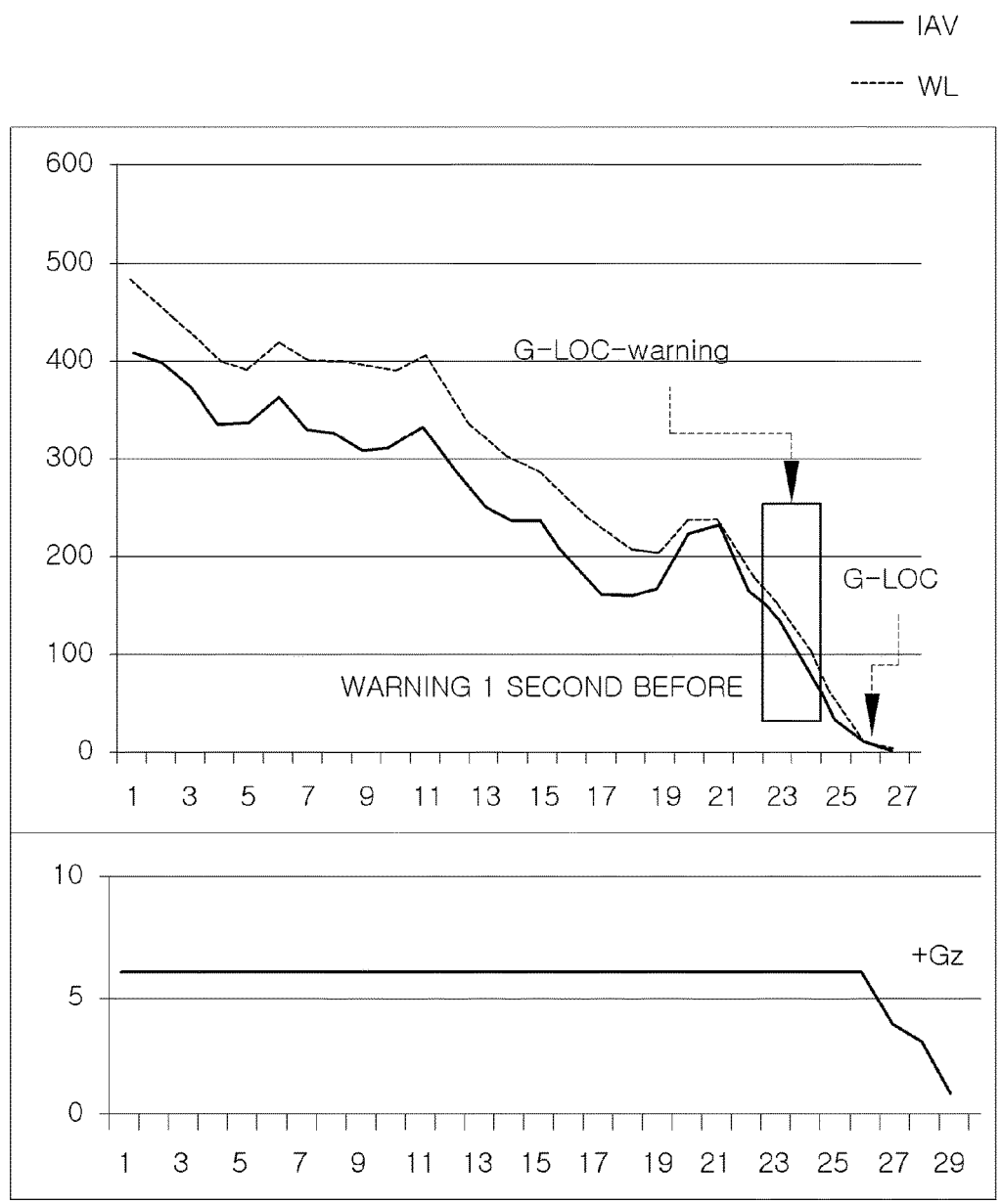
Figure 8F:
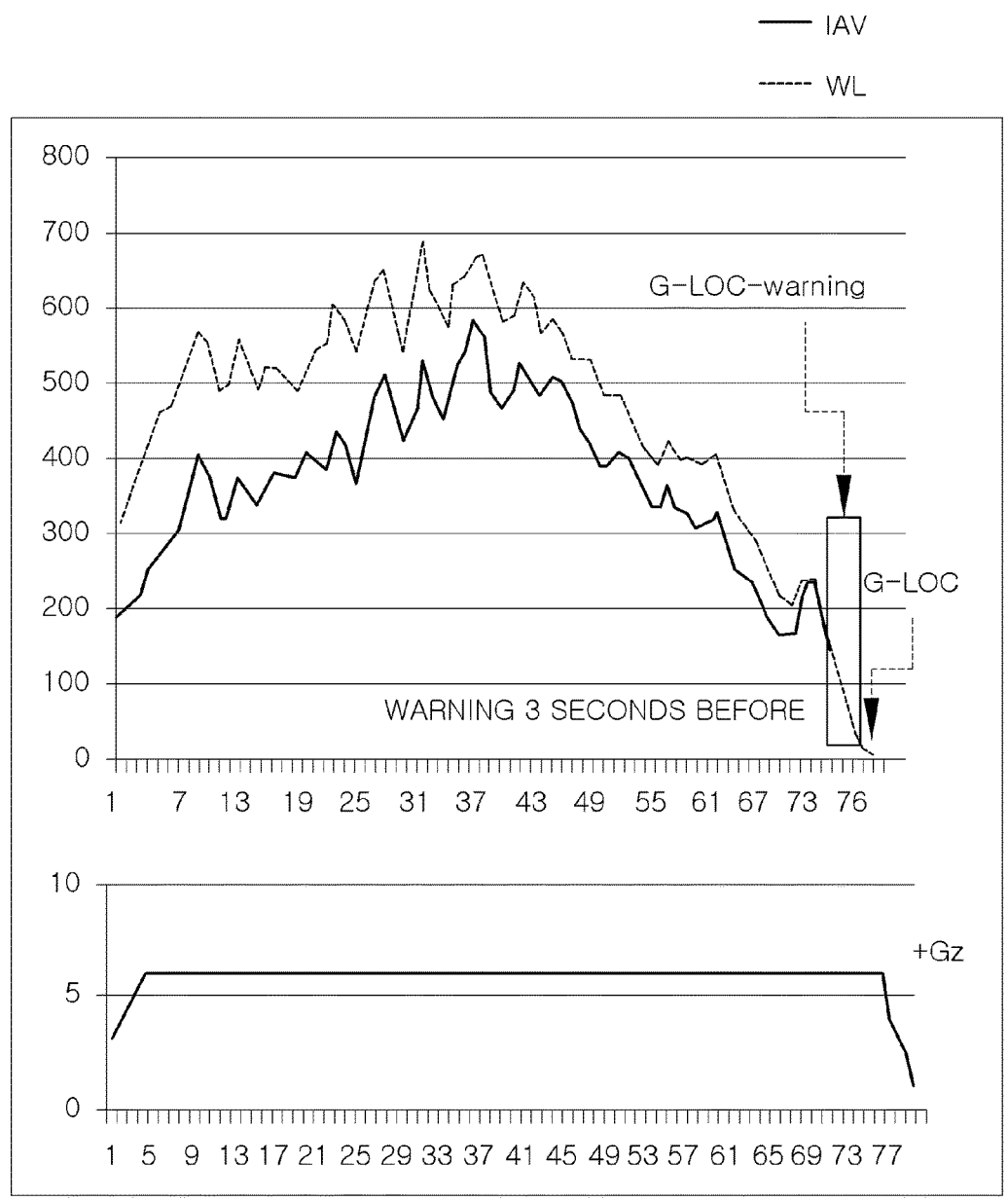

Among these examples, FIG. 8C shows the case in which the subject spontaneously recovers (by self-recovery) after the first warning signal is generated, and does not enter a G-LOC state, but the risk of G-LOC is determined again through continuous monitoring and the G-LOC warning signal sounds again 3.5 seconds before entering a G-LOC state.

As described above, the present invention provides the method for preventing accidents attributable to G-LOC through the analysis of an EMG signal. According to the method, because a G-LOC state may be continuously predicted in real time using the G-LOC warning algorithm, and because the G-LOC may be quickly detected in early stages, an aircraft may be induced to fly safely before crashing, whereby the incidence of aircraft accidents may be reduced and the lives of aircraft pilots may be saved.

The invention claimed is:

1. A gravity-induced loss of consciousness (G-LOC) warning method, comprising:
   measuring an electromyogram (EMG) signal of a muscle using an EMG sensor and storing the EMG signal;
   setting reference values to an initial reaction value of an integrated absolute value (IAV) and an initial reaction value of a waveform length (WL), calculated based on an initial EMG signal, which is measured for a certain time period from a start of measurement of the EMG signal, and storing the reference values;
   monitoring the EMG signal in real time using the EMG sensor, calculating the IAV, the WL, a change in a slope of the IAV, and a change in a slope of the WL from the monitored EMG signal, as indication values, and storing the indication values; and
   comparing the reference values with the indication values determining that the slope of the IAV and the slope of the WL, calculated in real time, decrease N successive times and that each of a measured IAV and WL is equal to or less than a certain percentage of the reference value thereof, and ascertaining based on the determining that a risk of G-LOC exists, wherein a warning signal is generated based on the ascertaining.

2. The G-LOC warning method of claim 1, wherein determining includes determining that each of the IAV and the WL, measured in real time, is equal to or less than the certain percentage of the reference value thereof N successive times.

3. The G-LOC warning method of claim 2, wherein N is 3.

4. The G-LOC warning method of claim 1, wherein the measuring starts at 5G or higher acceleration.

5. The G-LOC warning method of claim 1, wherein the setting the reference values comprises:
   calculating the initial reaction value of the IAV and the initial reaction value of the WL based on the initial EMG signal, measured for the certain time period from the start of the measurement of the EMG signal; and
   calculating and recording an average of the initial reaction value of the IAV and an average of the initial reaction value of the WL.

6. A gravity-induced loss of consciousness (G-LOC) warning method, comprising:
   measuring an electromyogram (EMG) signal of a muscle using an EMG sensor and storing the EMG signal;
   setting reference values to an initial reaction value of an integrated absolute value (IAV) and an initial reaction value of a waveform length (WL), calculated based on an initial EMG signal, measured for a certain time period from a start of measurement of the EMG signal, and storing the reference values;
   monitoring the EMG signal in real time using the EMG sensor, calculating the IAV, the WL, and changes in slopes of the IAV and WL from the monitored EMG signal, as indication values, and storing the indication values; and
   comparing the reference values with the indication values, determining that each of the IAV and the WL, measured in real time, is equal to or less than a certain percentage of the reference value thereof N successive times, and ascertaining based on the determining that a risk of G-LOC exists, wherein a warning signal is generated based on the ascertaining.

7. The G-LOC warning method of claim 6, wherein determining includes determining that a slope of the IAV and a slope of the WL, calculated in real time, decrease N successive times and that each of the measured IAV and WL is equal to or less than the certain percentage of the reference value thereof.

8. The G-LOC warning method of claim 7, wherein N is 3.

9. The G-LOC warning method of claim 6, wherein the measuring starts at 5G or higher acceleration.

10. The G-LOC warning method of claim 6, wherein the setting the reference values comprises:
- calculating the initial reaction value of the IAV and the initial reaction value of the WL based on the initial EMG signal, measured for the certain time period from the start of the measurement of the EMG signal; and
- calculating and recording an average of the initial reaction value of the IAV and an average of the initial reaction value of the WL.

11. A gravity-induced loss of consciousness (G-LOC) warning system, comprising:
- a sensor unit, including an EMG sensor, for measuring an EMG signal by being affixed on a part of a body of a user;
- a control unit for setting reference values using an initial reaction value of an integrated absolute value (IAV) and an initial reaction value of a waveform length (WL) based on the measured EMG signal, for calculating the IAV, the WL, a change in a slope of the IAV, and a change in a slope of the WL as indication values by monitoring the EMG signal in real time using the EMG sensor, and for determining whether a risk of G-LOC exists through a series of determination processes using the reference values and the indication values;
- a display unit for receiving the EMG signal and displaying an action potential of the EMG signal; and
- a warning unit for receiving a warning signal.

12. The G-LOC warning system of claim 11, wherein when the slope of the IAV and the slope of the WL, calculated in real time, decrease N successive times and when each of a measured IAV and WL is equal to or less than a certain percentage of the reference value thereof, the control unit determines that the risk of G-LOC exists and outputs the warning signal to the warning unit.

13. The G-LOC warning system of claim 12, wherein if each of the IAV and the WL, measured in real time, is equal to or less than the certain percentage of the reference value thereof N successive times, the control unit determines that the risk of G-LOC exists and outputs the warning signal to the warning unit.

14. The G-LOC warning system of claim 11, wherein when each of the IAV and the WL, measured in real time, is equal to or less than the certain percentage of the reference value thereof N successive times, the control unit determines that the risk of G-LOC exists and outputs the warning signal to the warning unit.

15. The G-LOC warning system of claim 14, wherein if the slope of the IAV and the slope of the WL, calculated in real time, decrease N successive times and if each of the measured IAV and WL is equal to or less than the certain percentage of the reference value thereof, the control unit determines that the risk of G-LOC exists and outputs the warning signal to the warning unit.

* * * * *